(12) United States Patent
Suehara

(10) Patent No.: US 8,936,612 B2
(45) Date of Patent: Jan. 20, 2015

(54) MEDICAL TREATMENT TOOL

(75) Inventor: Satoru Suehara, Ashigarakami-gun (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 0 days.

(21) Appl. No.: 14/006,594

(22) PCT Filed: Jul. 18, 2012

(86) PCT No.: PCT/JP2012/068180
§ 371 (c)(1),
(2), (4) Date: Sep. 20, 2013

(87) PCT Pub. No.: WO2014/013565
PCT Pub. Date: Jan. 23, 2014

(65) Prior Publication Data
US 2014/0031853 A1 Jan. 30, 2014

(51) Int. Cl.
*A61M 29/00* (2006.01)
*A61M 29/02* (2006.01)
(Continued)

(52) U.S. Cl.
CPC ............... *A61M 29/02* (2013.01); *A61B 17/24* (2013.01); *A61M 25/0138* (2013.01); *A61M 25/0147* (2013.01); *A61B 1/0055* (2013.01); *A61B 1/0057* (2013.01); *A61M 2025/1065* (2013.01); *A61M 2025/1093* (2013.01); *A61B 1/00082* (2013.01); *A61B 1/00135* (2013.01); *A61B 2017/00314* (2013.01)
USPC ........................................................ 606/192

(58) Field of Classification Search
CPC ............ A61M 25/10; A61M 25/1006; A61M 25/1018; A61M 25/104; A61M 25/0147; A61M 25/0138; A61M 2025/1065

USPC ................ 606/191, 192, 194, 199; 604/96.01
See application file for complete search history.

(56) References Cited

U.S. PATENT DOCUMENTS 7,632,242 B2 * 12/2009 Griffin et al. ............... 604/96.01
2005/0148997 A1 * 7/2005 Valley et al. .................. 604/509
(Continued)

FOREIGN PATENT DOCUMENTS

| JP | 5-293077 A | 11/1993 |
| JP | 6-142209 A | 5/1994 |

(Continued)

OTHER PUBLICATIONS

International Search Report (PCT/ISA/210) mailed on Sep. 18, 2012, by the Japanese Patent Office as the International Searching Authority for International Application No. PCT/JP2012/068180.
(Continued)

*Primary Examiner* — Katherine Dowe
(74) *Attorney, Agent, or Firm* — Buchanan Ingersoll & Rooney PC

(57) ABSTRACT

A medical treatment tool includes: an insert portion at least a part of which is provided by a flexing portion that is adapted to be flexed, the insert portion being adapted to be inserted into a human body of a patient; and an inflatable body provided on an outer circumference of the flexing portion, the inflatable body being inflated in a radial direction of the flexing portion. An axial distal end portion of the inflatable body is fixed to the insert portion while a proximal end portion of the inflatable body is axially movable relative to the insert portion.

11 Claims, 12 Drawing Sheets

(51) Int. Cl.
 *A61B 17/24* (2006.01)
 *A61M 25/01* (2006.01)
 *A61B 1/005* (2006.01)
 *A61M 25/10* (2013.01)
 *A61B 1/00* (2006.01)
 *A61B 17/00* (2006.01)

(56) References Cited

U.S. PATENT DOCUMENTS

| | | | |
|---|---|---|---|
| 2005/0228438 | A1 | 10/2005 | Sachar et al. |
| 2009/0131867 | A1* | 5/2009 | Liu et al. ............... 604/96.01 |
| 2010/0217185 | A1* | 8/2010 | Terliuc et al. ........... 604/96.01 |
| 2010/0312338 | A1 | 12/2010 | Gonzales et al. |

FOREIGN PATENT DOCUMENTS

| | | |
|---|---|---|
| JP | 10-165507 A | 6/1998 |
| JP | 2003-117003 A | 4/2003 |
| JP | 2004-528126 A | 9/2004 |
| JP | 2006-509597 A | 3/2006 |
| JP | 2009-056297 A | 3/2009 |
| JP | 2009-517124 A | 4/2009 |
| JP | 2009-526610 A | 7/2009 |
| WO | WO 02/096483 A2 | 12/2002 |
| WO | WO 2004/060434 A2 | 7/2004 |
| WO | WO 2007/095125 A2 | 8/2007 |

OTHER PUBLICATIONS

Written Opinion (PCT/ISA/237) mailed on Sep. 18, 2012, by the Japanese Patent Office as the International Searching Authority for International Application No. PCT/JP2012/068180.

Office Action (Notice of Reason(s) for Rejection) issued on Nov. 12, 2013, by the Japanese Patent Office in corresponding Japanese Patent Application No. 2013-540168, and an English Translation of the Office Action. (4 pages).

* cited by examiner

MEDICAL TREATMENT TOOL

TECHNICAL FIELD

The present invention relates to a medical treatment tool.

BACKGROUND ART

Medical treatment tools that include a flexible insert portion to be inserted into a human body and an inflatable body provided on an outer circumference of the insert portion have been typically known (see, for instance, Patent Literature 1).

The medical treatment tool disclosed in Patent Literature 1 includes a shaft having a flexible joint portion (flexing portion) provided at an end thereof, an inflatable body provided on an outer circumference of the joint portion, and a channel provided along the shaft to be in communication with the inflatable body. The inflatable body is inflatable in a radial direction of the insert portion by a fluid introduced into the inflatable body through the channel.

CITATION LIST

Patent Literature(s)

Patent Literature 1 US 2010/0312338 A

SUMMARY OF INVENTION

Problems to be Solved by the Invention

However, when the flexing portion of the typically known medical treatment tool as disclosed in Patent Literature 1 is flexed, the inflatable body is pulled in an axial direction of the insert portion, resulting in a deformation of the inflatable body. Thus, the inflatable body cannot be inflated or, on the contrary, a pressure within the inflatable body becomes excessively high to cause a deformation of the flexing portion.

An object of the invention is to provide a medical treatment tool that is capable of appropriately inflating an inflatable body provided to a flexing portion.

Means for Solving the Problems

A medical treatment tool according to an aspect of the invention includes: an insert portion that is adapted to be inserted to a human body of a patient, at least a part of the insert portion being provided by a flexing portion adapted to be flexed; and an inflatable body provided on an outer circumference of the flexing portion, the inflatable body being adapted to inflate in a radial direction of the flexing portion. An axial distal end portion of the inflatable body is fixed to the insert portion and a proximal end portion of the inflatable body is axially movable relative to the insert portion.

According to the above aspect of the invention, when the flexing portion is flexed, since the proximal end portion of the inflatable body is axially moved relative to the insert portion, the deformation of the inflatable body can be avoided. Thus, the inflatable body can be appropriately inflated.

The medical treatment tool according to the above aspect preferably includes a shape retainer that is adapted to retain a shape of the flexing portion after the flexing portion is flexed.

According to the above arrangement, since the shape retainer is provided, the shape of the flexing portion after being subjected to the flexing operation can be retained by the shape retainer. Thus, since the shape of the flexing portion can be retained in accordance with an insertion path of the insert portion in a human body of a patient, the inflatable body provided to the flexing portion can be easily inserted into the human body.

In the medical treatment tool according to the above aspect, the shape retainer preferably includes: a joint structure in which a plurality of joints are connected, the joint structure defining the flexing portion; and a manipulation member provided inside the joint structure, the manipulation member controlling a flexure of the flexing portion.

According to the above arrangement, since the shape retainer includes the joint structure defining the flexing portion and the manipulation member provided inside the joint structure, the manipulation member can be accommodated inside the joint structure, so that the manipulation member can be kept from being caught in a human body of a patient. Further, since the flexing portion has the joint structure, an operation force required for the flexing operation of the flexing portion using the manipulation member can be reduced. Accordingly, the insert portion can be easily inserted into the human body and the inserted insert portion can be easily flexed.

In the medical treatment tool according to the above aspect, the insert portion preferably includes therein a lumen adapted to receive therein and draw therefrom a treatment tool.

According to the above arrangement, since the insert portion has the lumen, a treatment tool can be introduced through the lumen of the insert portion inserted into a human body of a patient, so that the treatment tool can be easily inserted into the human body.

The medical treatment tool according to the above aspect preferably includes a slide member fixed to the proximal end portion of the inflatable body, the slide member being adapted to seal the inflatable body and being slidable relative to the insert portion.

According to the above arrangement, since the proximal end portion of the inflatable body is fixed to the slide member that is capable of sealing the inflatable body, the proximal end portion of the inflatable body can be moved relative to the insert portion in conjunction with the slide movement of the slide member while the inflatable body is kept sealed.

In the medical treatment tool according to the above aspect, the slide member is preferably a tubular member, and the tubular member preferably includes: a slide portion fixed to the proximal end portion of the inflatable body and slidable relative to the insert portion; and a flexible portion including a first end in an axial direction of the tubular member being connected to the slide portion and a second end being fixed to the insert portion.

According to the above arrangement, since the slide member is provided by the tubular member having the flexible portion and the slide portion, the proximal end portion of the inflatable body can be moved relative to the insert portion in conjunction with the slide movement of the slide portion while the flexible portion absorbs the deformation of the tubular member resulting from the flexing of the insert portion.

In the medical treatment tool according to the above aspect, the slide member is preferably a sealing member fixed to the proximal end portion of the inflatable body to seal a gap between the proximal end portion and the insert portion.

According to the above arrangement, since the slide member is provided by the sealing member for sealing the gap between the proximal end portion of the inflatable body and the insert portion, the proximal end portion of the inflatable body can be moved relative to the insert portion in conjunction with the slide movement of the sealing member while the inflatable body is securely sealed.

In the medical treatment tool according to the above aspect, the proximal end portion of the inflatable body preferably has a stretchable part that is stretchable and contractible in an axial direction of the inflatable body, a part of the proximal end portion closer to a proximal end than the stretchable part being fixed to the insert portion.

According to the above arrangement, since the proximal end portion of the inflatable body is stretchable and contractible, when the flexing portion is flexed, the proximal end portion of the inflatable body axially stretches to allow a movement of the proximal end portion of the inflatable body relative to the insert portion.

In the medical treatment tool according to the above aspect, the proximal end portion of the inflatable body is preferably folded toward the distal end portion of the inflatable body to be fixed to the insert portion.

According to the above arrangement, since the proximal end portion of the inflatable body is folded toward the distal end, when flexing the flexing portion, the folded portion of the inflatable body is gradually unfolded to elongate the proximal end portion of the inflatable body. Thus, the proximal end portion of the inflatable body can be moved relative to the insert portion, so that the inflatable body can be appropriately inflated.

In the medical treatment tool according to the above aspect, a movement assisting member for assisting an axial movement of the inflatable body is preferably connected to the proximal end portion of the inflatable body.

According to the above arrangement, since the movement assisting member is connected to the proximal end portion of the inflatable body, the movement of the proximal end portion of the inflatable body can be assisted by the movement assisting member, thereby easily moving the proximal end portion in the axial direction of the insert portion.

In the medical treatment tool according to the above aspect, the medical treatment tool is preferably a treatment tool for treating sinusitis.

According to the above arrangement, since the medical treatment tool is a paranasal sinus treatment tool and the inflatable body of the paranasal sinus treatment tool can be appropriately inflated, a stenosed area formed in a natural ostium of paranasal sinus due to sinusitis can be widened by the inflatable body for treatment.

DESCRIPTION OF EMBODIMENT(S)

Figure 1:
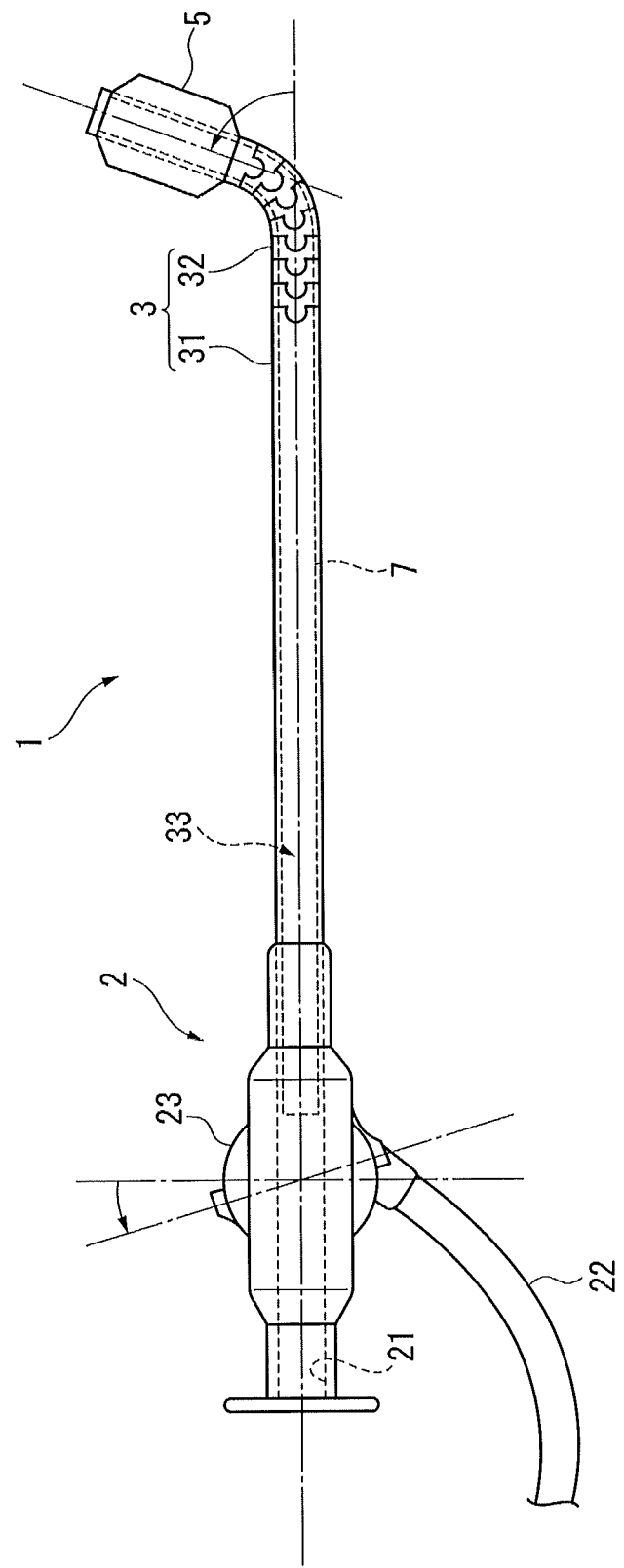
FIG. 1 is a plan view showing a medical treatment tool according to a first exemplary embodiment of the invention.

Exemplary embodiments of the invention will be described below with reference to the attached drawings.

It should be noted that components in the second and subsequent exemplary embodiments that are the same as or functionally similar to components in the following first exemplary embodiment will be denoted by the same reference numerals as those of the first exemplary embodiment to omit or simplify the explanation thereof.

First Exemplary Embodiment

As shown in FIG. 1, a medical treatment tool 1 includes: a hub 2; an insert portion in a form of an insertion tube 3 that is at least partially flexible and is to be inserted into a human body of a patient; a movable portion 4 (see FIGS. 2 and 3) provided on an outer circumference of the insertion tube 3 and axially movable relative to the insertion tube 3; an inflatable body 5 provided on the outer circumference of the insertion tube 3 and inflatable in a radial direction of the insertion tube 3; a fluid transportation channel 6 that transports a fluid to an inside of the inflatable body 5 (see FIGS. 2 and 3); and a manipulation member 7 provided inside the insertion tube 3 for controlling the flexure of the insertion tube 3.

The hub 2 includes: an introduction channel 21 that intercommunicates a lumen 33 in the insertion tube 3 with an outside to allow a treatment tool such as an endoscope to be introduced into the lumen 33; a fluid transportation channel 22 that is branched from the introduction channel 21 so as to transport a fluid such as normal saline into a human body and to transport a fluid in the human body to the outside; and a position fixing unit 23 that is rotatably provided to the hub 2, the position fixing unit 23 fixing a posture of the insertion tube 3 flexed by the manipulation member 7.

Figure 2:
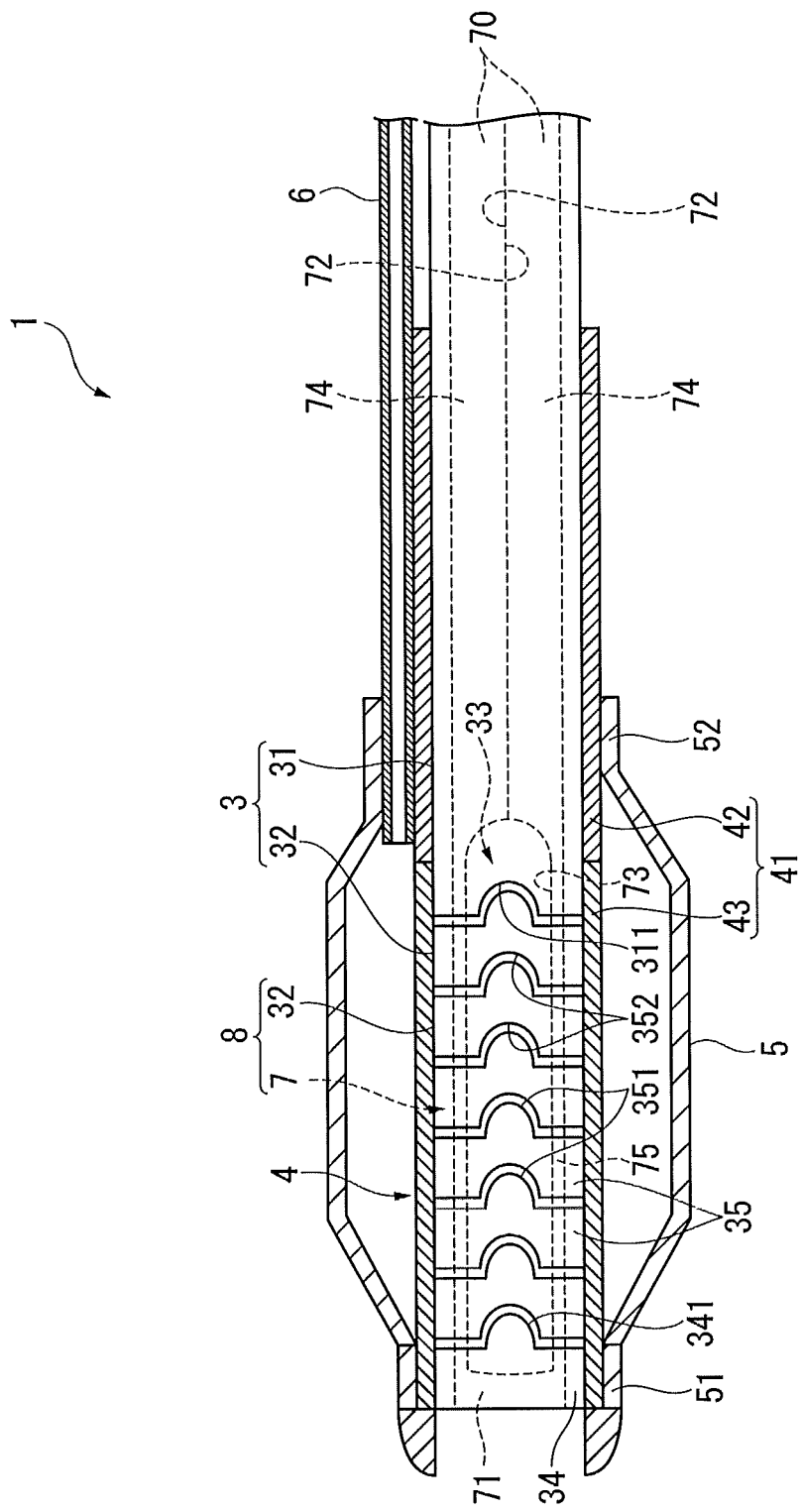
FIG. 2 is a partially-sectioned side elevation showing an insertion tube of the medical treatment tool shown in FIG. 1.
Figure 3:
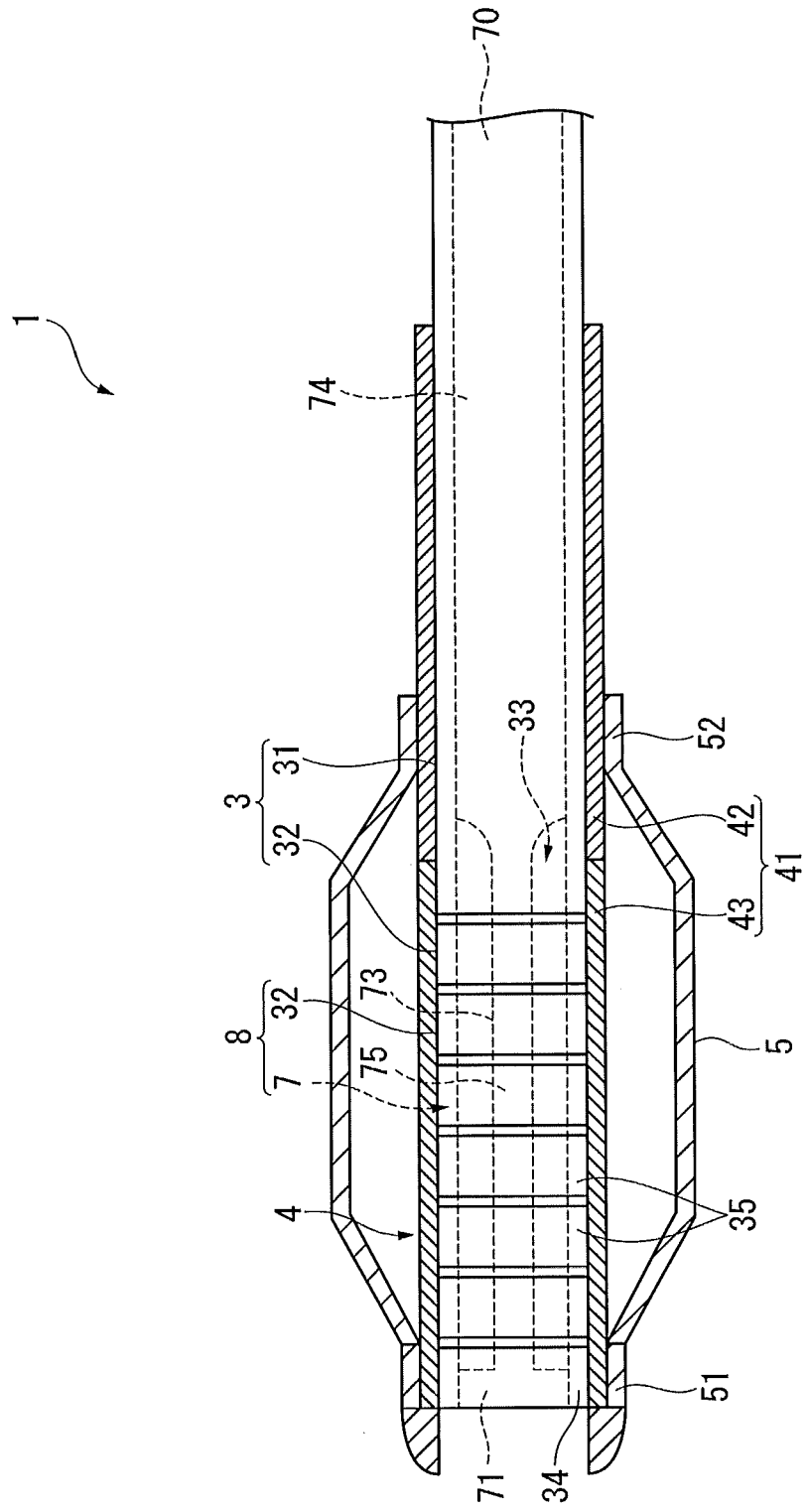
FIG. 3 is another partially-sectioned side elevation showing the insertion tube of the medical treatment tool shown in FIG. 1.

As shown in FIGS. 2 and 3, the insertion tube 3 includes: a rigid tube 31 whose axial proximal end is connected to the hub 2; a flexing portion in a form of a flexible tube 32 connected to an axial distal end of the rigid tube 31; and the lumen 33 (a continuous space in the rigid tube 31 and the flexible tube 32) being adapted to receive therein and draw therefrom a treatment tool such as an endoscope.

The flexible tube 32 includes a plurality of tubular bodies 34 and 35. The tubular bodies 34 and 35 and the rigid tube 31 are axially connected to provide a joint structure in a mutually pivotable manner.

The tubular bodies 34 and 35 respectively include a pivot shaft 341 and a pivot shaft 351, each of which respectively projects in a connecting direction (i.e. an axial direction of each of the tubular bodies 34 and 35) from a first end thereof in the connecting direction.

On the other hand, the rigid tube 31 and the tubular bodies 35 respectively include a pivot support 311 and a pivot support 352, each of which is defined by a recess formed in a second end in the connecting direction (i.e. the axial direction of the rigid tube 31 and the tubular bodies 35). The pivot support 311 supports the pivot shaft 351 of the tubular body 35 while the pivot support 352 support the pivot shaft 341 of the tubular body 34.

It should be noted that the pivot shaft 341 and the pivot shaft 351 are provided in pairs and the pivot support 311 and the pivot support 352 are provided in pairs at positions symmetrical with each other around central axes of the rigid tube 31 and the tubular bodies 34 and 35.

The above-described insertion tube 3 is provided by, for instance, laser-processing of a stainless cylindrical member. With the use of the laser-processing, the insertion tube 3 with the rigid tube 31 and the tubular bodies 34 and 35 being connected can be easily obtained only by cutting the cylindrical member with laser. It should be understood that any material and process other than those mentioned above can be used for producing the insertion tube 3.

The movable portion 4 is provided by a slide member in a form of a tubular member 41 that covers the outer circumference of the insertion tube 3. The tubular member 41 is capable of sealing the inflatable body 5 and sliding relative to the insertion tube 3.

The tubular member 41 includes a slide portion 42 that is fixed to an axial proximal end portion 52 of the inflatable body 5 and is slidable relative to the insertion tube 3 and a flexible portion 43 having an axial first end connected to the slide portion 42 and an axial second end fixed to the insertion tube 3.

The slide portion 42 is provided by a member of an excellent slip property such as a metal and a resin and is slidable on the outer circumference of the rigid tube 31.

The flexible portion 43 is provided by a flexible elastic member such as a rubber and a resin and is provided on the outer circumference of the flexible tube 32. An axial distal end of the flexible portion 43 is fixed to the insertion tube 3 whereas a proximal end of the flexible portion 43 is continuous with the slide portion 42. The flexible portion 43 closely covers the outer circumference of the flexible tube 32 to keep the fluid delivered to the inflatable body 5 from entering the flexible tube 32 through the gaps between the tubular body 34 and the tubular body 35, between the tubular bodies 35 and between the tubular body 35 and the rigid tube 31.

The inflatable body 5 is provided by an elastic material such as a polymer plastic. An axial distal end portion 51 of the inflatable body 5 is fixed to the insertion tube 3 whereas the proximal end portion 52 of the inflatable body 5 is fixed to the slide portion 42. Thus, the proximal end portion 52 of the inflatable body 5 is axially movable relative to the insertion tube 3 via the slide portion 42. The interior of the inflatable body 5 is in communication with the fluid transportation channel 6. The fluid is introduced into the inflatable body 5 through the fluid transportation channel 6 to radially inflate the inflatable body 5.

The fluid transportation channel 6 is provided along the insertion tube 3. A distal end of the fluid transportation channel 6 is connected to the proximal end portion 52 of the inflatable body 5 to be in communication with the interior of the inflatable body 5. A proximal end of the fluid transportation channel 6 is connected to the position fixing unit 23 (FIG. 1) so as to be axially movable in the axial direction of the insertion tube 3 in conjunction with the proximal end portion 52 of the inflatable body 5.

Figure 4:
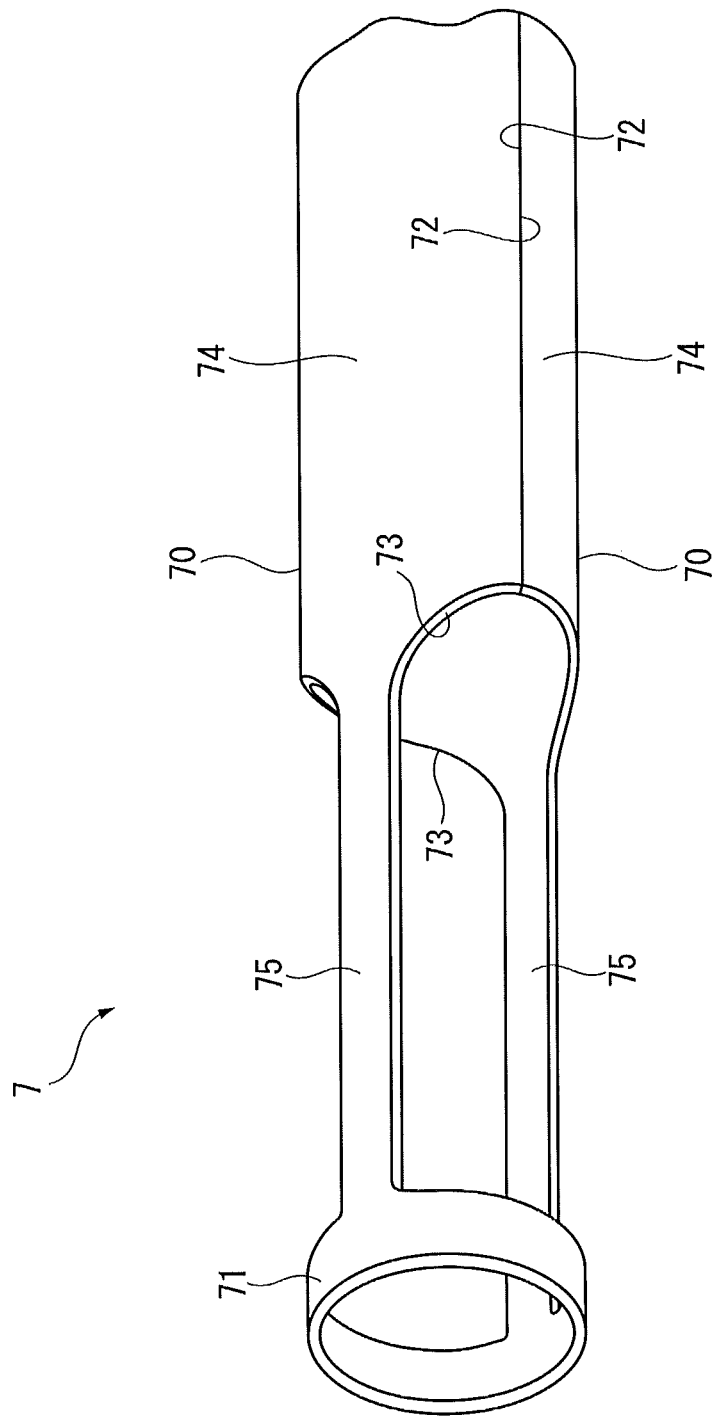
FIG. 4 is a perspective view of a manipulation member of the medical treatment tool shown in FIG. 1.

As also shown in FIG. 4, the manipulation member 7 includes: a plurality of separable members 70 that are circumferentially dividable and collectively form a tubular structure in the insertion tube 3; and an annular connecting portion 71 that connects respective axial distal ends of the separable members 70 in the tubular structure.

Each of the plurality of separable members 70 is of the same shape. Each of the separable members 70 includes: a cutout portion 73 provided by partially cutting a circumferential side edge 72 of the separable member 70; a wide portion 74 at which the cutout 73 of the separable member 70 is not provided, the wide portion being defined in a form of a circumferentially divided cylindrical member; and a narrow portion 75 at which the cutout portion 73 of the separable member 70 is provided, the narrow portion 75 being narrower than the wide portion 74 by the presence of the cutout portion 73.

The cutout portion 73 is provided by cutting each of both the circumferential side edges 72 at the same axial position into the same shape. It should be noted that, in the first exemplary embodiment, the cutout portion 73 is defined at a section between the connecting portion 71 and the wide portion 74.

The wide portion 74 is provided by circumferentially bisecting the cylindrical member. The circumferential side edge 72 of the wide portion 74 is of linear configuration and is axially in slidable contact with the side edge 72 of the adjacent separable member 70. In other words, the separable members 70 are designed such that the circumferential side edges 72 thereof (i.e. other than the cutout portion 73) are axially in slidable contact with each other.

The narrow portion 75 axially extends approximately at the circumferential center of each of the separable members 70 and has a constant circumferential dimension. The narrow portions 75 of the separable members 70 each are provided at positions opposed across the center of the tubular structure.

One of the separable members 70 and the other of the separable members 70 of the manipulation member 7 are relatively moved in the axial direction, so that the opposed two narrow portions 75 are flexed in a plane passing the two narrow portions 75 to flex the flexible tube 32. Thus, the manipulation member 7 is disposed in the insertion tube 3 so that the narrow portions 75 are located between the mutually opposing pivot shafts 341 and 351 of the flexible tube 32, or, in other words, the cutout portions 73 are located at the positions of the pivot shafts 341 and 351.

Herein, in order to increase an inner diameter of the lumen 33 of the insertion tube 3, an outer diameter of the manipulation member 7 is preferably as large as possible. Thus, the manipulation member 7 is sized such that an outer surface of the manipulation member 7 is in contact with an inner surface of the insertion tube 3.

Further, for the similar reason, the thickness of the manipulation member 7 is preferably as small as possible. Thus, the thickness of the manipulation member 7 is designed to be approximately 0.05 to 1.0 [mm], preferably 0.075 to 0.3 [mm].

Similarly to the insertion tube 3, the above-described manipulation member 7 is provided by, for instance, laser-processing of a stainless cylindrical member. It should be understood that any material and process other than those mentioned above can be used for producing the manipulation member 7.

The manipulation member 7 and the flexible tube 32 define a shape retainer 8 that is adapted to retain a shape of the flexible tube 32 after a flexing operation.

Figure 5:
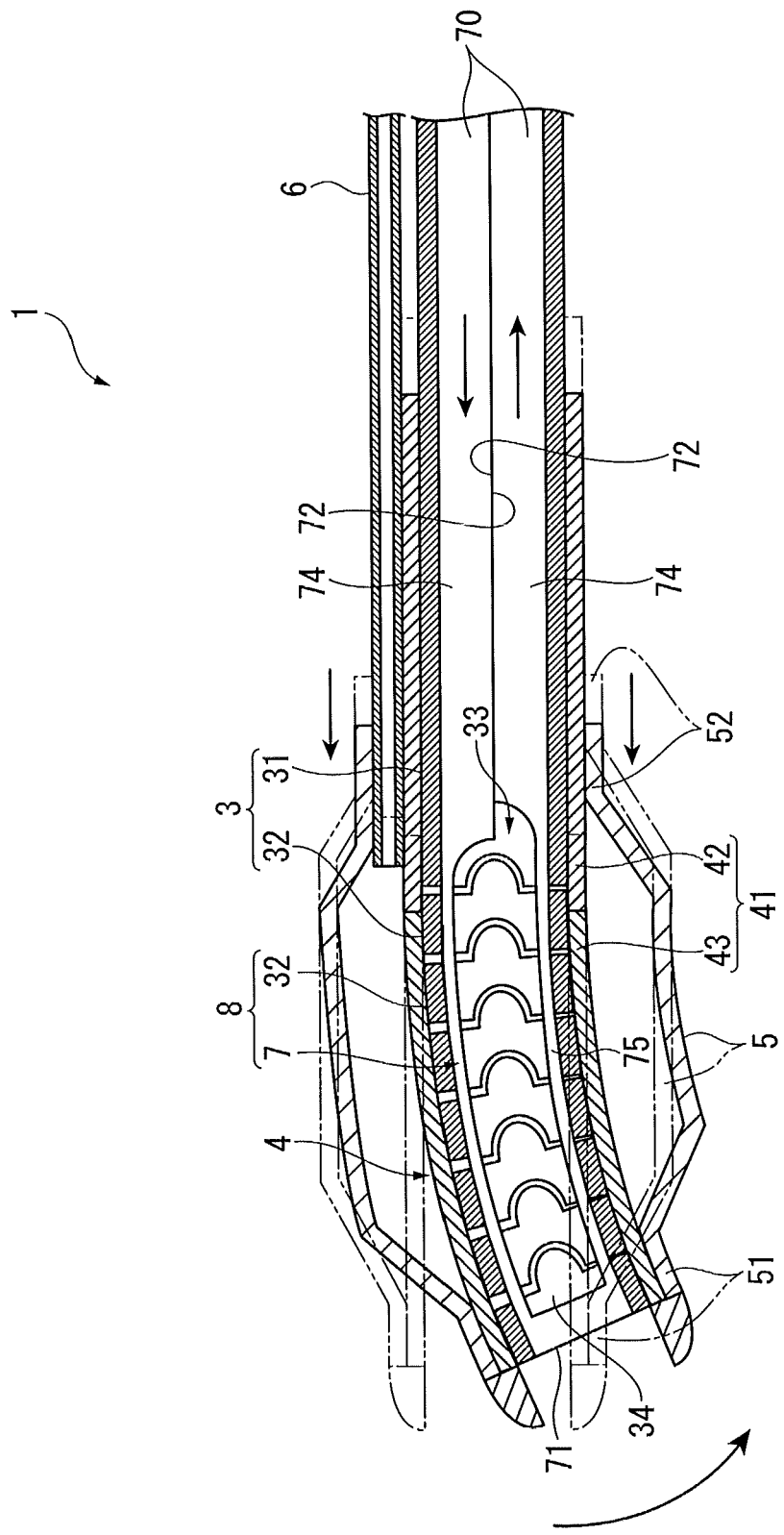
FIG. 5 is a side elevation showing a flexed state of the insertion tube of the medical treatment tool shown in FIG. 1.

The position fixing unit 23 is rotated relative to the hub 2 for flexing the flexible tube 32 of the insertion tube 3 in the above medical treatment tool 1. When the position fixing unit 23 is rotated, as shown in FIG. 5, one of the separable members 70 of the manipulation member 7 is pushed toward the distal end while the other of the separable members 70 is pulled toward the proximal end. As a result, while the adjacent circumferential side edges 72 of the separable members 70 are axially slid, an axial and relative movement occurs between the one of the separable members 70 and the other of the separable members 70. Thus, the flexible tube 32 can be flexed in accordance with the flexure of the narrow portion 75 of the manipulation member 7 while the outer surface of the manipulation member 7 is in slidable contact with the inner surface of the insertion tube 3. It should be noted that the flexed posture of the flexible tube 32 at this time can be fixed by the position fixing unit 23.

The inflatable body 5 is designed such that only the distal end portion 51 is fixed to the insertion tube 3 while the proximal end portion 52 of the inflatable body 5 is axially movable relative to the insertion tube 3 via the slide portion 42 of the tubular member 41. Thus, when the flexible tube 32 is flexed, the inflatable body 5 is pulled in the axial direction of the insertion tube 3, so that, as shown in FIG. 5, the proximal end portion 52 moves toward the distal end of the insertion tube 3. As a result, since the deformation of the inflatable body 5 can be avoided, when the inflatable body 5 is inflated while the flexible tube 32 is flexed, the inflatable body 5 can be appropriately inflated.

Next, the process and advantages of using the medical treatment tool 1 in a form of a sinusitis treatment tool will be described below as an example of the usage of the medical treatment tool 1.

Initially, an operator inserts the insertion tube 3 of the medical treatment tool 1 into a nostril. At this time, when an imaging unit such as an endoscope is inserted in the insertion tube 3 in advance, the operator can insert the insertion tube 3 while checking the status inside the insertion path based on image information acquired by the imaging unit.

When the inflatable body 5 of the inserted insertion tube 3 reaches a natural ostium of a paranasal sinus stenosed by sinusitis, the operator introduces a fluid into the inflatable body 5 through the introduction channel 21 to widen the inflatable body 5 to inflate the stenosed area in the natural ostium for treatment. It should be noted that whether or not the stenosed area is widened can be checked based on the image information acquired by the imaging unit by slightly retracting the insertion tube 3 after contracting the inflatable body 5.

When the paranasal sinus is filled with a fluid (e.g. snivel) and/or a viscous substance, the insertion tube 3 is inserted into the paranasal sinus through the widened natural ostium for transferring the fluid and/or the viscous substance through the inner cavity of the insertion tube 3 and the fluid transportation channel 22. In addition, a washing fluid such as normal saline may be introduced in the fluid transportation channel 22 for washing the interior of the paranasal sinus with the fluid.

The first exemplary embodiment exemplarily offers the following advantages.

When the flexible tube 32 is flexed, since the proximal end portion 52 of the inflatable body 5 is axially moved relative to the insertion tube 3, the deformation of the inflatable body 5 can be avoided. Thus, the inflatable body 5 can be appropriately inflated.

Since the shape retainer 8 is provided, the shape of the flexible tube 32 after the flexing operation can be retained by the shape retainer 8. Thus, since the shape of the flexible tube 32 can be retained in accordance with the insertion path of the insertion tube 3 in a human body of a patient, the inflatable body 5 provided to the flexible tube 32 can be easily inserted into the human body.

Since the shape retainer 8 includes the joint structure constituting the flexible tube 32 and the manipulation member 7 provided inside the joint structure and the manipulation member 7 can be accommodated inside the joint structure, the manipulation member 7 can be kept from being caught in a human body of a patient. Further, since the flexible tube 32 has the joint structure, an operation force required for the flexing operation of the flexible tube 32 using the manipulation member 7 can be reduced. As a result, the insertion tube 3 can be easily inserted into the human body and the inserted insertion tube 3 can be easily flexed.

Since the insertion tube 3 has the lumen 33, a treatment tool such as an endoscope can be introduced through the lumen 33 of the insertion tube 3 inserted into the human body, so that the treatment tool can be easily inserted into the human body.

Since the proximal end portion 52 of the inflatable body 5 is fixed to the slide portion 42 of the tubular member 41 that is capable of sealing the inflatable body 5, the proximal end portion 52 of the inflatable body 5 can be moved relative to the insertion tube 3 with the slide movement of the slide portion 42 while the inflatable body 5 is kept being sealed.

Since the slide member is provided by the tubular member 41 having the flexible portion 43 and the slide portion 42, the proximal end portion 52 of the inflatable body 5 can be moved relative to the insertion tube 3 in conjunction with the slide movement of the slide portion 42 while the flexible portion 43 absorbs the deformation of the tubular member 41 in accordance with the flex of the insertion tube 3.

Further, when the medical treatment tool 1 is a paranasal sinus treatment tool, the inflatable body 5 of the paranasal sinus treatment tool can be appropriately inflated. Accordingly, the stenosed area formed in the natural ostium of paranasal sinus due to sinusitis can be widened by the inflatable body 5 for treatment.

Second Exemplary Embodiment

Next, a second exemplary embodiment of the invention will be described below with reference to FIG. 6.

Figure 6:
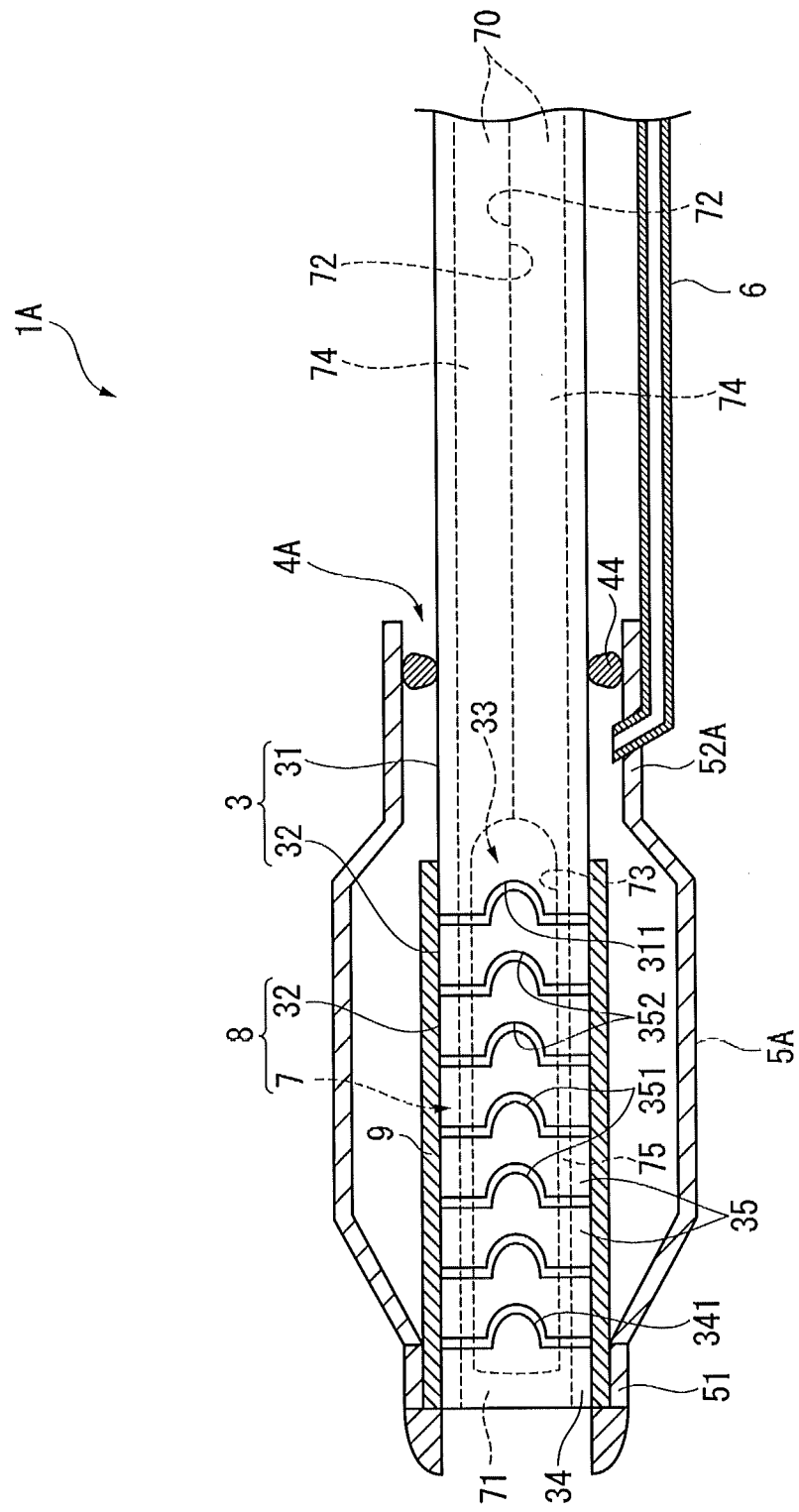
FIG. 6 is a side elevation showing an insertion tube of a medical treatment tool according to a second exemplary embodiment of the invention.

As shown in FIG. 6, a medical treatment tool 1A according to the second exemplary embodiment differs from the first exemplary embodiment in the presence of a slide member in a form of a sealing member 44 provided between a proximal end portion 52A of an inflatable body 5A and the insertion tube 3, and in the structure of a movable portion 4A.

The sealing member 44 is an annular member provided between the proximal end portion 52A of the inflatable body 5A and the insertion tube 3. The sealing member 44 seals a gap between the proximal end portion 52A and the insertion tube 3. The sealing member 44 is slidable relative to the insertion tube 3 in conjunction with the proximal end portion 52A of the inflatable body 5A. The fluid transportation channel 6 is connected to a part of the proximal end portion 52A closer to the distal end than the sealing member 44 so that the fluid transportation channel 6 is movable in the axial direction of the insertion tube 3 in conjunction with the proximal end portion 52A. As described above, in the second exemplary embodiment, the proximal end portion 52A of the inflatable body 5A is movable relative to the insertion tube 3 via the sealing member 44 and the sealing member 44 defines the movable portion 4A.

It should be noted that the flexible tubular member 9 (e.g. an elastic member) of the medical treatment tool 1A closely covers the outer circumference of the flexible tube 32 to keep the fluid delivered to the inflatable body 5A from entering the interior of the flexible tube 32 through the gaps between the tubular body 34 and the tubular body 35, between the tubular bodies 35 and between the tubular body 35 and the rigid tube 31.

The second exemplary embodiment exemplarily offers the following advantages in addition to the advantages of the first exemplary embodiment.

Since the slide member is provided by the sealing member 44 for sealing the gap between the proximal end portion 52A of the inflatable body 5A and the insertion tube 3, the proximal end portion 52A of the inflatable body 5A can be moved relative to the insertion tube 3 in conjunction with the slide movement of the sealing member 44 while the inflatable body 5A is securely sealed.

Third Exemplary Embodiment

Next, a third exemplary embodiment of the invention will be described below with reference to FIG. 7.

Figure 7:
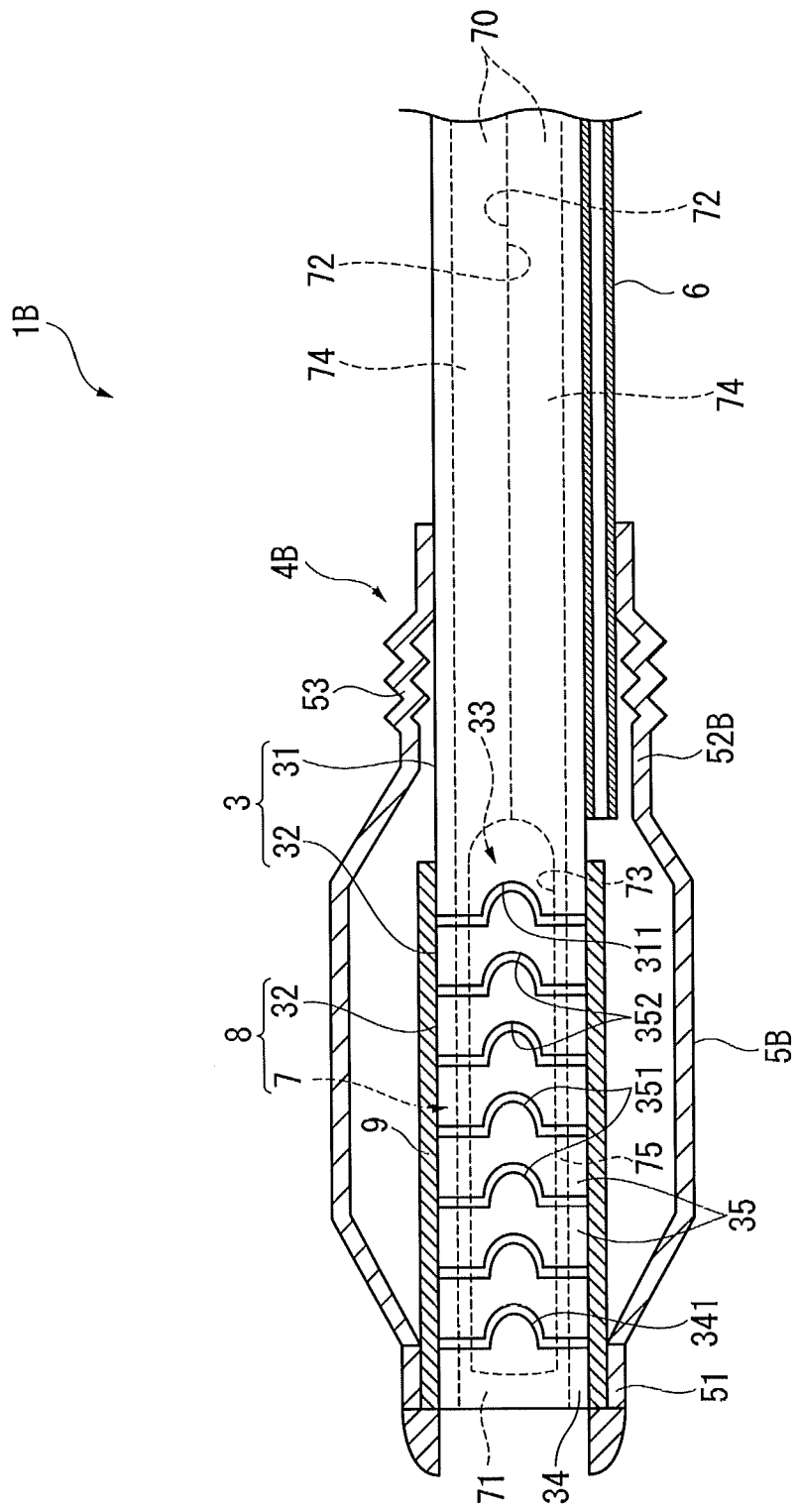
FIG. 7 is a side elevation showing an insertion tube of a medical treatment tool according to a third exemplary embodiment of the invention.

As shown in FIG. 7, a medical treatment tool 1B according to the third exemplary embodiment differs from the first exemplary embodiment in the presence of an axially stretchable and contractible proximal end portion 52B of an inflatable body 5B and in the structure of a movable portion 4B.

The proximal end portion 52B of the inflatable body 5B is in a form of a bellows. A part of the proximal end portion 52B near the proximal end relative to the bellows 53 is fixed to the rigid tube 31. In the third exemplary embodiment, the proximal end portion 52B of the inflatable body 5B is movable relative to the insertion tube 3 in conjunction with stretch and contraction of the bellows 53 and the bellows 53 of the proximal end portion 52B defines the movable portion 4B. It should be noted that the fluid transportation channel 6 is fixed to the rigid tube 31 and to a part of the proximal end portion 52B near the proximal end relative to the bellows 53 so as to be immovable relative to the insertion tube 3.

The third exemplary embodiment exemplarily offers the following advantages in addition to the advantages of the first exemplary embodiment.

Since the proximal end portion 52B of the inflatable body 5B is stretchable and contractible, when the flexible tube 32 is flexed, the proximal end portion 52B of the inflatable body 5B axially stretches to allow a movement of the proximal end portion 52B of the inflatable body 5B relative to the insertion tube 3.

Fourth Exemplary Embodiment

Next, a fourth exemplary embodiment of the invention will be described below with reference to FIG. 8.

Figure 8:
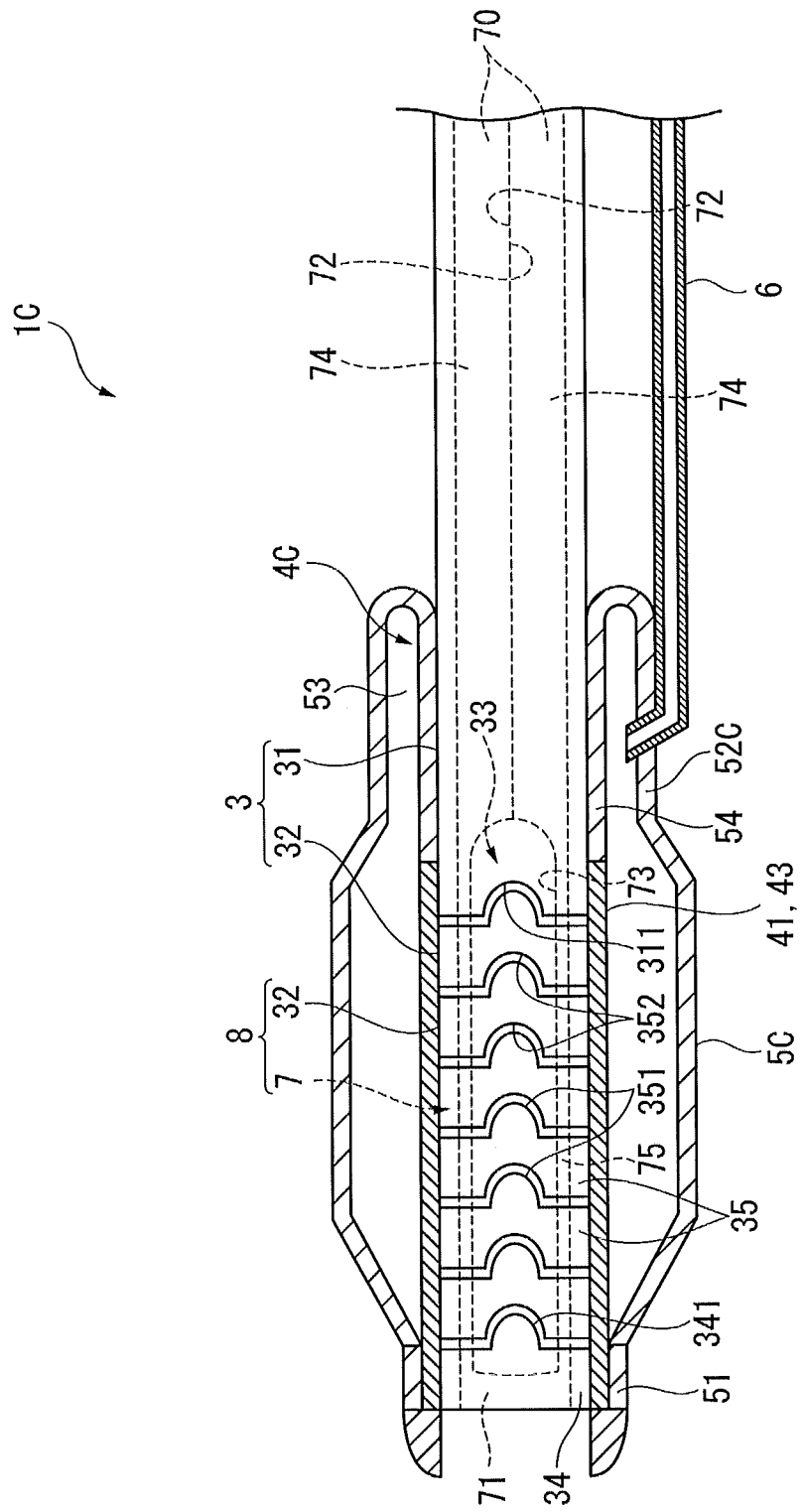
FIG. 8 is a side elevation showing an insertion tube of a medical treatment tool according to a fourth exemplary embodiment of the invention.

As shown in FIG. 8, a medical treatment tool 1C according to the fourth exemplary embodiment differs from the first exemplary embodiment in a proximal end portion 52C of an inflatable body 5C that is folded toward the distal end portion 51 to be fixed to the insertion tube 3 and in the structure of a movable portion 4C.

The proximal end portion 52C of the inflatable body 5C is folded toward the distal end portion 51 to form a folded portion 54. The folded portion 54 is connected to the flexible portion 43 of the tubular member 41. The slide portion 42 is not provided to the tubular member 41. The folded portion 54 is fixed to the insertion tube 3 via the tubular member 41. In the fourth exemplary embodiment, the proximal end portion 52C of the inflatable body 5C is movable relative to the insertion tube 3 by the presence of the folded portion 54 and the folded portion 54 and the flexible portion 43 of the tubular member 41 define the movable portion 4C. The fluid transportation channel 6 is connected to the proximal end portion 52C of the inflatable body 5C. The fluid transportation channel 6 is movable in the axial direction of the insertion tube 3 in conjunction with the proximal end portion 52C.

The fourth exemplary embodiment exemplarily offers the following advantages in addition to the advantages of the first exemplary embodiment.

Since the proximal end portion 52C of the inflatable body 5C is folded toward the distal end portion 51, when the flexible tube 32 is flexed, the folded portion 54 of the inflatable body 5C is gradually unfolded to elongate the proximal end portion 52C of the inflatable body 5C. Thus, the proximal end portion 52C of the inflatable body 5C can be moved relative to the insertion tube 3, so that the inflatable body 5C can be appropriately inflated.

Fifth Exemplary Embodiment

Next, a fifth exemplary embodiment of the invention will be described below with reference to FIG. 9.

Figure 9:
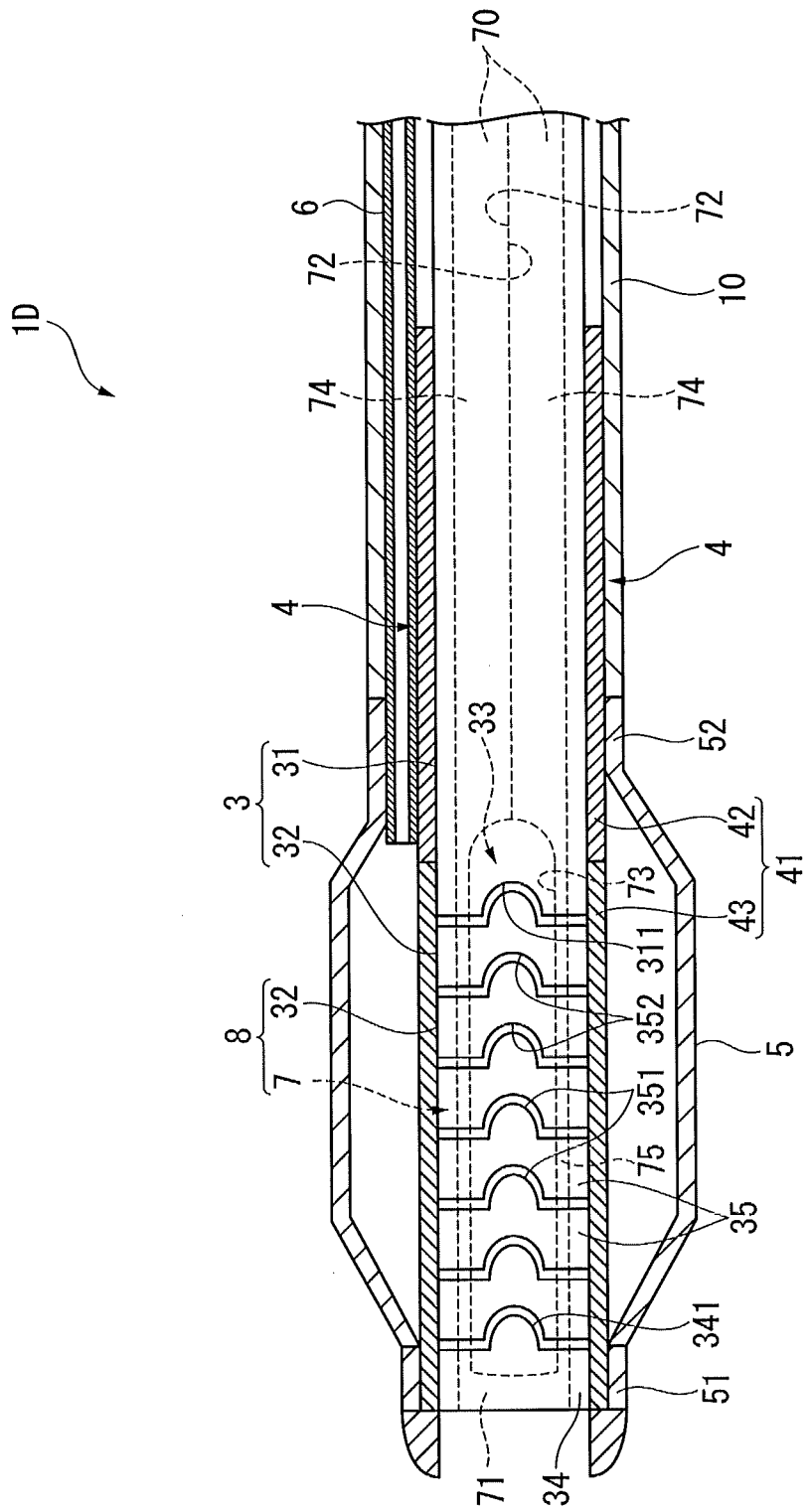
FIG. 9 is a side elevation showing an insertion tube of a medical treatment tool according to a fifth exemplary embodiment of the invention.

As shown in FIG. 9, a medical treatment tool 1D according to the fifth exemplary embodiment differs from the first exemplary embodiment in that a movement assisting member 10 is connected to the proximal end portion 52 of the inflatable body 5.

The movement assisting member 10 is provided by a member of an excellent slip property such as a metal and a resin. The movement assisting member 10 extends on an outside of the insertion tube 3 in the axial direction of the insertion tube 3. A distal end of the movement assisting member 10 is fixed to the inflatable body 5, the tubular member 41 and the fluid transportation channel 6. Thus, the movement of the inflatable body 5 relative to the insertion tube 3 can be assisted by moving the movement assisting member 10 in the axial direction of the insertion tube 3.

The fifth exemplary embodiment exemplarily offers the following advantages in addition to the advantages of the first exemplary embodiment.

Since the movement assisting member 10 is connected to the proximal end portion 52 of the inflatable body 5, the movement of the proximal end portion 52 of the inflatable body 5 can be assisted by the movement assisting member 10, thereby easily moving the proximal end portion 52 in the axial direction of the insertion tube 3.

Sixth Exemplary Embodiment

Next, a sixth exemplary embodiment of the invention will be described below with reference to FIG. 10.

Figure 10:
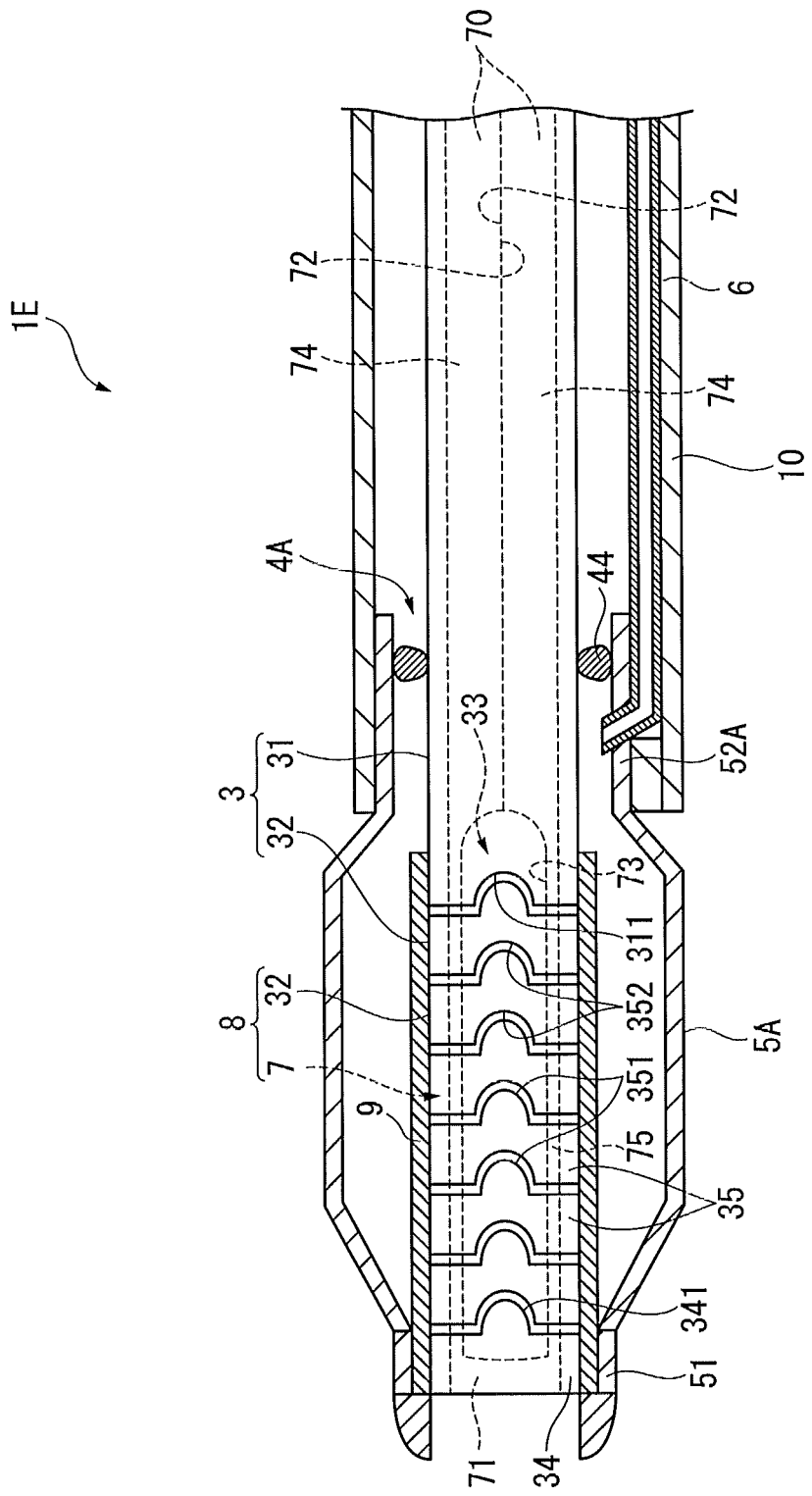
FIG. 10 is a side elevation showing an insertion tube of a medical treatment tool according to a sixth exemplary embodiment of the invention.

As shown in FIG. 10, a medical treatment tool 1E according to the sixth exemplary embodiment differs from the second exemplary embodiment in that the movement assisting member 10 is connected to the proximal end portion 52A of the inflatable body 5A.

The movement assisting member 10 extends in the axial direction of the insertion tube 3. The distal end of the movement assisting member 10 is connected to the proximal end portion 52A of the inflatable body 5A. The fluid transportation channel 6 is provided between the movement assisting member 10 and the insertion tube 3. The distal end of the fluid transportation channel 6 is connected to a part of the proximal end portion 52A of the inflatable body 5A closer to the distal end than the sealing member 44.

The sixth exemplary embodiment exemplarily offers the advantages in the fifth exemplary embodiment in addition to the advantages of the second exemplary embodiment.

Seventh Exemplary Embodiment

Next, a seventh exemplary embodiment of the invention will be described below with reference to FIG. 7.

Figure 11:
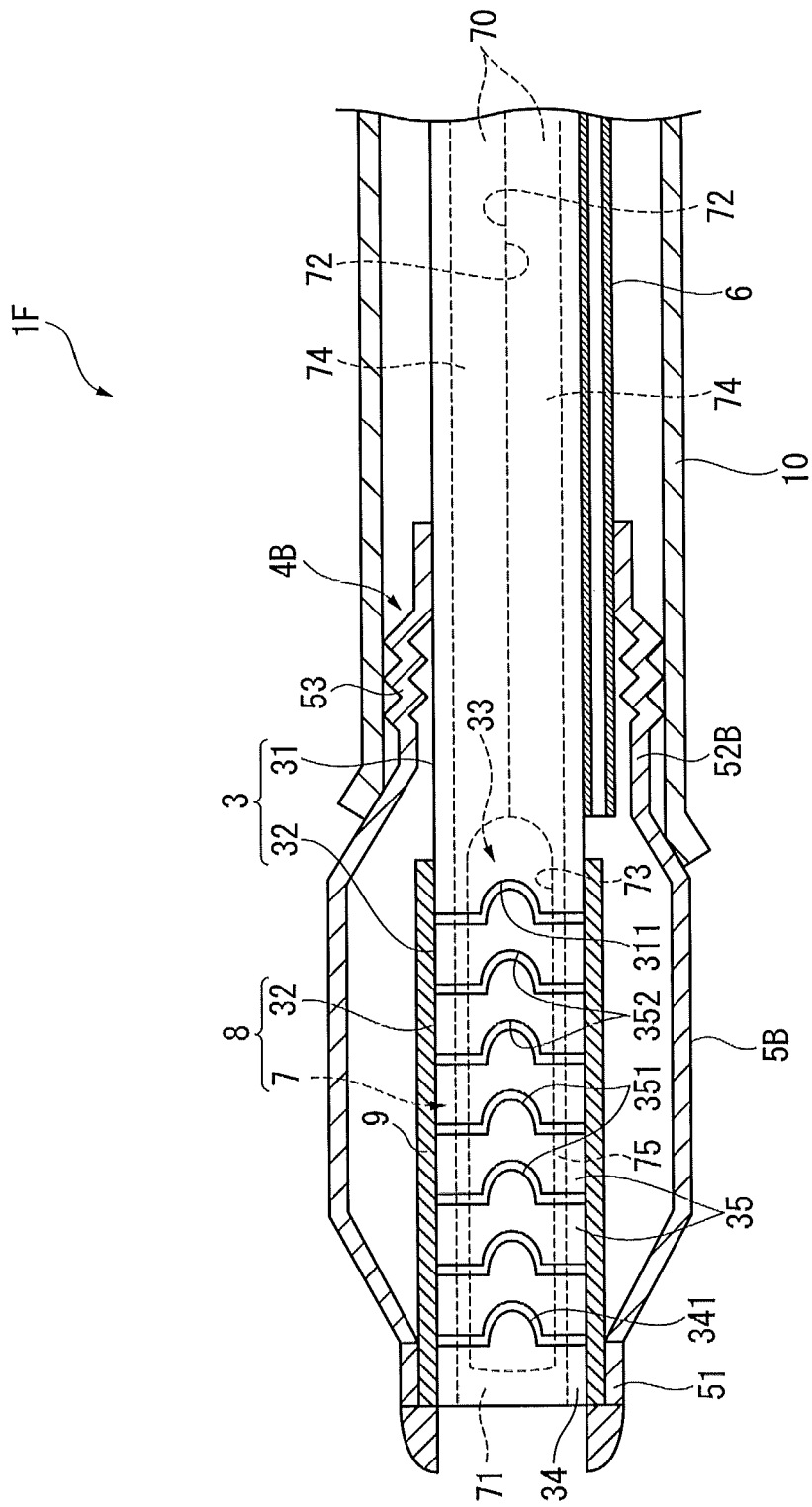
FIG. 11 is a side elevation showing an insertion tube of a medical treatment tool according to a seventh exemplary embodiment of the invention.

As shown in FIG. 11, a medical treatment tool 1F according to the seventh exemplary embodiment differs from the third exemplary embodiment in that the movement assisting member 10 is connected to the proximal end portion 52B of the inflatable body 5B.

The movement assisting member 10 extends in the axial direction of the insertion tube 3. The distal end of the movement assisting member 10 is connected to a part of the proximal end portion 52B of the inflatable body 5B closer to the proximal end than the bellows 53.

The seventh exemplary embodiment exemplarily offers the advantages in the fifth exemplary embodiment in addition to the advantages of the third exemplary embodiment.

Eighth Exemplary Embodiment

Next, an eighth exemplary embodiment of the invention will be described below with reference to FIG. 12.

Figure 12:
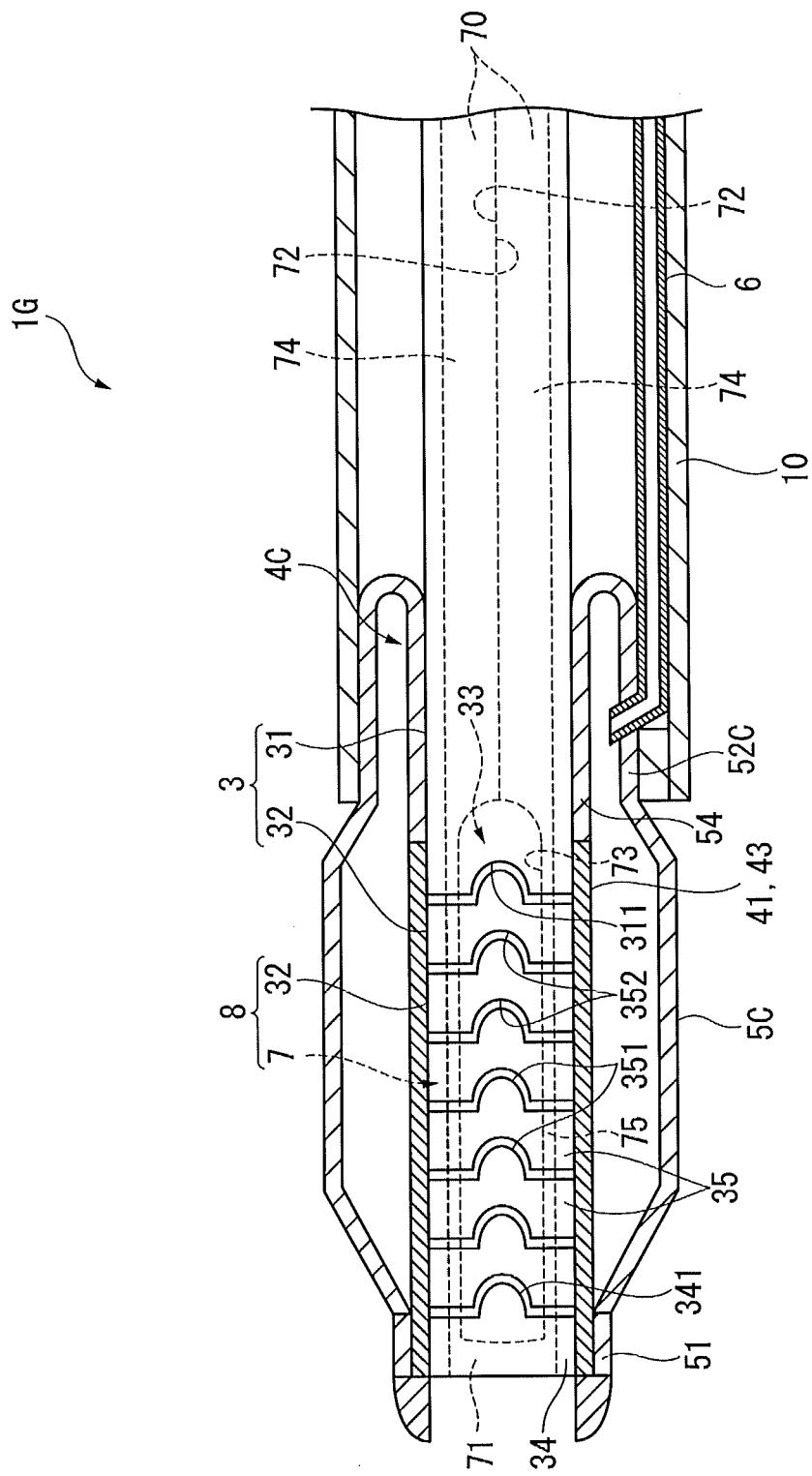
FIG. 12 is a side elevation showing an insertion tube of a medical treatment tool according to an eighth exemplary embodiment of the invention.

As shown in FIG. 12, a medical treatment tool 1G according to the eighth exemplary embodiment differs from the fourth exemplary embodiment in that the movement assisting member 10 is connected to the proximal end portion 52C of the inflatable body 5C.

The eighth exemplary embodiment exemplarily offers the advantages in the fifth exemplary embodiment in addition to the advantages of the fourth exemplary embodiment.

Incidentally, it should be understood that the scope of the present invention is not limited to the above-described exemplary embodiments but includes modifications and improvements as long as the modifications and improvements are compatible with the invention.

For instance, though the insertion tube 3 is used as the insert portion and the flexible tube 32 is used as the flexing portion in the above exemplary embodiments, the insert portion and the flexing portion are not necessarily be tubular but may be solid.

Any member is usable as the insertion tube 3 as long as at least a part of the member is flexible. For instance, an insertion tube 3 of which entirety is flexible may be used instead of the insertion tube 3 provided with the flexible tube 32 in the above exemplary embodiments, or a partially flexible insertion tube 3 may alternatively be used. Alternatively, an insertion tube 3 of which entirety is provided by the flexible tube 32 may be used. The insertion tube 3 is not necessarily cylindrical but may have a polygonal cross section.

Though the insertion tube 3 and the manipulation member 7 are made of metal such as stainless, the insertion tube 3 and the manipulation member 7 may be made of other materials including a resin and metal other than stainless as long as the material is flexible.

Though the manipulation member 7 includes the separable members 70 that are divided into two or four pieces, the number of the divided pieces of the separable members is not limited to two or four as long as a plurality of (i.e. two or more) pieces are provided.

The shape of the connecting portion 71 of the manipulation member 7 is not limited to that in the above exemplary embodiments but the connecting portion 71 may alternatively have a tubular or linear shape. Further alternatively, the connecting portion 71 may be provided by a plurality of linear members that define bridges between the separable members 70 so that the plurality of linear members intersects at a central axis of the tubular structure of the manipulation member 7.

Though the fluid transportation channel 6 in the above exemplary embodiments is provided outside and along the insertion tube 3, the fluid transportation channel 6 may alternatively be provided outside the insertion tube 3 concentrically with the insertion tube 3.

Though the medical treatment tools 1 and 1A to 1G in the above exemplary embodiments are used for inspecting an interior of a paranasal sinus, widening a stenosed area in a natural ostium of a paranasal sinus and treating sinusitis, the medical treatment tools 1 and 1A to 1G may alternatively be used for inspecting and treating the other parts inside a human body.

The invention claimed is:

1. A medical treatment tool comprising:
an insert portion that is adapted to be inserted to a human body of a patient, at least a part of the insert portion being provided by a flexing portion adapted to be flexed;
an inflatable body provided on an outer circumference of the flexing portion, the inflatable body being adapted to inflate in a radial direction of the flexing portion;
a slide member axially slidable relative to the insert portion, the slide member being tubular; wherein
the flexing portion is provided by a joint structure in which a plurality of joints are connected;
the slide member seals the inflatable body and covers the joint structure;
a distal end portion of the slide member is fixed to the insert portion and a proximal end portion of the slide member is fixed to an axial proximal end portion of the inflatable body; and
an axial distal end portion of the inflatable body is fixed to the insert portion and the proximal end portion of the inflatable body is axially movable relative to the insert portion.

2. The medical treatment tool according to claim 1, further comprising:
a shape retainer that is adapted to retain a shape of the flexing portion after the flexing portion is flexed.

3. The medical treatment tool according to claim 2, wherein
the shape retainer comprises:
the joint structure; and
a manipulation member provided inside the joint structure, the manipulation member controlling a flexure of the flexing portion.

4. The medical treatment tool according to claim 1, wherein
the insert portion comprises therein a lumen adapted to receive therein and draw therefrom a treatment tool.

5. The medical treatment tool according to claim 1, wherein
the slide member
comprises:
a slide portion fixed to the proximal end portion of the inflatable body and slidable relative to the insert portion; and
a flexible portion comprising a first end in an axial direction of the slide member being connected to the slide portion and a second end being fixed to the insert portion.

6. The medical treatment tool according to claim 5, wherein
the flexing portion of the insert portion includes a gap between axially adjacent pairs of the plurality of joints, and
the flexible portion of the slide member seals the gap.

7. The medical treatment tool according to claim 1, wherein
a movement assisting member for assisting an axial movement of the inflatable body is connected to the proximal end portion of the inflatable body.

8. The medical treatment tool according to claim 1, wherein
the medical treatment tool is a treatment tool for treating sinusitis.

9. The medical treatment tool according to claim 1, further comprising:
a manipulation member inside the joint structure, the manipulation member controlling a fixture of the flexing portion, wherein
the insert portion possesses a lumen adapted to receive a treatment tool, the treatment tool being configured to be withdrawn from the lumen, and
the manipulation member is a tubular structure and defines a part of the lumen.

10. The medical treatment tool according to claim 1, wherein
the flexing portion includes a gap between axially adjacent pairs of the plurality of joints.

11. A medical treatment tool comprising:
an insert portion configured to be inserted into a human body of a patient, at least a part of the insert portion being a flexing portion configured to be flexed;
an inflatable body provided on an outer circumference of the flexing portion, the inflatable body being inflatable in a radial direction of the flexing portion, the inflatable body possessing an axial distal end portion and an axial proximal end portion;
a tubular slide portion surrounding the insert portion and axially slidable relative to the insert portion, the tubular slide portion possessing a distal-most end;
a tubular flexible portion surrounding the flexing portion of the insert portion and positioned axially distal of the distal-most end of the tubular slide portion;
the tubular flexible portion being fixed to the insert portion so that the tubular flexible portion and the insert portion move together;
the flexing portion being comprised of axially arranged tubular bodies, with axially adjacent ones of the tubular bodies being connected to each other so that the tubular bodies together form a joint structure;
the tubular flexible portion covering the joint structure;
the tubular slide portion being fixed to the axial proximal end portion of the inflatable body;
the axial distal end portion of the inflatable body being fixed to the insert portion; and
the proximal end portion of the inflatable body being axially movable relative to the insert portion.

* * * * *